United States Patent [19]

Kernes et al.

[11] Patent Number: 4,932,948

[45] Date of Patent: Jun. 12, 1990

[54] MALE EXTERNAL CATHETER AND ANTIMICROBIAL INSERT THEREFOR

[75] Inventors: Mary E. Kernes, Zion; Emil Stempel, Northbrook; Kenneth E. Riedel, Naperville, all of Ill.

[73] Assignee: Hollister Incorporated, Libertyville, Ill.

[21] Appl. No.: 172,769

[22] Filed: Mar. 28, 1988

[51] Int. Cl.$^5$ .............................. A61F 5/44
[52] U.S. Cl. ........................ 604/349; 128/844; 128/885
[58] Field of Search ............... 604/349–353, 604/265, 171; 128/885, 844

[56] References Cited

U.S. PATENT DOCUMENTS

| | | | |
|---|---|---|---|
| 2,789,560 | 4/1957 | Weimer | 604/349 |
| 2,838,045 | 6/1958 | Ryznar | 128/156 |
| 3,398,745 | 8/1968 | Tjerneld et al. | 604/349 |
| 3,848,603 | 11/1974 | Throner | 604/265 |
| 4,054,139 | 10/1977 | Crossley | 128/260 |
| 4,113,851 | 9/1978 | Leveen et al. | 424/28 |
| 4,310,509 | 1/1982 | Berglund et al. | 424/28 |
| 4,340,043 | 7/1982 | Seymour | 128/132 |
| 4,475,910 | 10/1984 | Conway et al. | 604/352 |
| 4,601,716 | 7/1986 | Smith | 604/351 |
| 4,626,250 | 12/1986 | Schneider | 604/352 |
| 4,640,688 | 2/1987 | Hauser | 604/352 |

OTHER PUBLICATIONS

Akiyama et al, Prophylaxis of Indwelling Urethral Catheter Infection J. of Urology, vol. 121, pp. 40–42, (1979).

*Primary Examiner*—Jerome L. Kruter
*Attorney, Agent, or Firm*—Tilton, Fallon, Lungmus

[57] ABSTRACT

A male external catheter having an insert of flexible plastic secured within the funnel-shaped end portion of the catheter. The insert reinforces the catheter's end portion and carries an antimicrobial agent to reduce risks of urinary tract infection for the wearer.

9 Claims, 1 Drawing Sheet

MALE EXTERNAL CATHETER AND ANTIMICROBIAL INSERT THEREFOR

Background

It has been estimated indwelling urethral catherization is performed in approximately 10 to 15% of hospitalized patients and that about one fourth of those contract bacterial infection of the urinary tract. Akiyama et al, Journal of Urology, Vol. 121: pp. 40–42 (1979). Prophylactic measures such as the application of antibiotic ointments and other bactericidal agents to the surfaces of such catheters may be useful, but a high incidence of urinary tract infection in long-term catherized patients remains a serious problem. Furthermore, while that problem is particularly severe for patients with internal catherization, a significant number of male patients subjected to external catherization also contract urinary infections.

External male catheters of various types are known in the medical field as disclosed, for example, in U.S. Pat. Nos. 4,626,250, 4,475,910, and 4,640,688. Characteristically, all of such catheters consist of a condom-like member formed of elastomeric material (usually latex rubber) having at least a drainage tube portion and an integral funnel portion communicating therewith. Such a catheter also usually includes a cylindrical body portion that fits about, and is adhesively secured to, the penile shaft of the wearer. In one particularly effective construction, the catheter includes an integral inner sleeve that is stretched over the glans and, among other things, protects the glans against prolonged contact with the small amounts of residual urine that often remain within a catheter worn by a nonambulatory patient.

As already indicated, efforts have been made in the past to reduce the risks of urinary tract infection for patients subjected to internal catherization by coating the catheter surfaces with bactericidal agents. For example, Foley catheters have been coated with silver powder and equipped with silver-plated connectors, and a reduction in bacteriuria has been observed by reason of the oligodynamic bactericidal property of silver ions. Akiyama et al, supra. U.S. Pat. No. 4,054,139 also discloses an indwelling catheter having surfaces coated with silver compounds. In U.S. Pat. No. 2,838,045, polymeric membranes are disclosed as being coated with antibiotic agents, with metallic ions having bactericidal properties, and with other antimicrobial agents such as phenyl mercuric acetate. Other patents disclosing antimicrobial compositions are U.S. Pat. Nos. 4,113,851, 4,340,043, and 4,310,509.

SUMMARY OF THE INVENTION

An important aspect of this invention lies in the discovery that the inclusion of an antimicrobial agent into or onto a conventional male external catheter presents complexities that may result in the deactivation of the agent by the latex additives or interfere with coagulation, or with the physical properties, of the latex, and in the further discovery that all of such problems may be overcome, and other important advantages may result, if such an antimicrobial agent were incorporated in a soft, flexible, plastic insert secured to the inside of the catheter directly in front of the glans. The insert is therefore located in the zone where small amounts of residual urine might be retained and in the flow path of urine discharged into the collection system. Of particular importance are the facts that the insert is located in close proximity to the glans and along the path of possible migration of bacteria from the collecting receptacle to the patient.

The plastic insert is generally cup-shaped, having an enlarged opening at its proximal end and a reduced opening at its distal end, and incorporates either on its surface or throughout its composition an antimicrobial agent capable of at least inhibiting bacterial growth in urine that contacts the surfaces of the insert. Optimally, the agent is bactericidal with respect to those strains known to cause a majority of urinary tract infections, namely, *Eschericheria Coli, Staphylococcus saphrophyticus, Staphylococcus epidermis,* and Klebsiella.

The insert is constructed so that it may be easily and quickly secured in place within the catheter sheath either at the time of manufacture or later at the time of use. Since the antimicrobial agent is carried by the insert, the physical properties of the catheter remain unaffected by that agent and, conversely, the bioactivity of the agent is generally unaffected by the composition of the catheter. Although soft and flexible, the insert nevertheless physically reinforces the catheter. Thus, where the construction of the catheter is intended to provide a spacing between the catheter's funnel portion and the glans of the wearer, the insert tends to prevent collapse of the funnel portion and prevent direct contact between that portion and the glans.

Means for securing the insert within the funnel portion of the catheter may take the form of an integral collar that projects into the catheter's drainage tube portion and engages that portion with sufficient force to prevent release of the insert. In a preferred construction, the collar flares outwardly into a bulbous enlargement or convolution of the catheter's drainge tube portion.

Other features, advantages, and objects of the invention will become apparent from the specification and drawings.

DRAWINGS

DETAILED DESCRIPTION OF PREFERRED EMBODIMENTS

Figure 1:
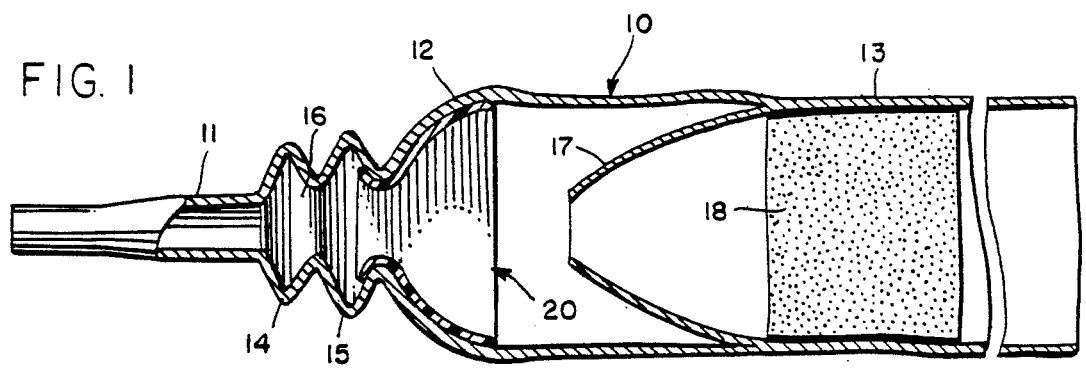
FIG. 1 is a longitudinal sectional view of an external male catheter equipped with an antimicrobial insert.
Figure 2:
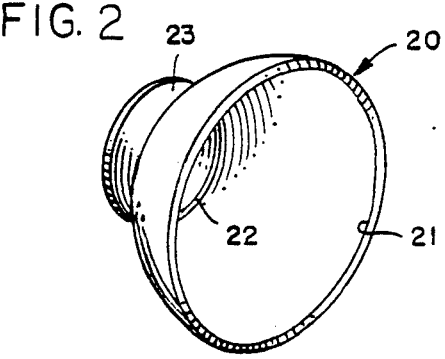
FIG. 2 is a perspective view showing the proximal side of the insert.
Figure 3:
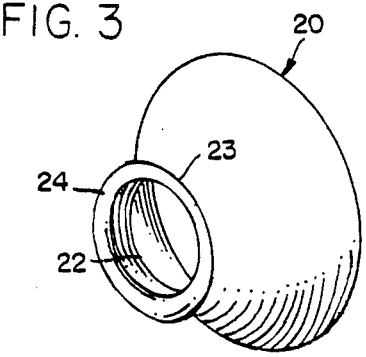
FIG. 3 is a perspective view depicting the insert's distal side.

Referring to the drawings, numeral 10 generally designates a male external catheter having a drainage tube portion 11, a tapered funnel portion 12 formed integrally therewith, and a generally cylindrical body portion 13. The drainage tube portion includes a pair of enlargements or convolutions 14 and 15 which define an expandable surge chamber 16 and also function to absorb longitudinal forces exerted on the drainage tube as well as prevent kinking of portion 11 in response to laterally-deflecting and/or twisting forces. The catheter also includes an inner sleeve portion 17 formed integrally with the cylindrical body portion 13. A pressure-sensitive adhesive layer 18 lines a portion of the cylindrical body directly behind sleeve 17 and, as disclosed in co-owned U.S. Pat. No. 4,626,250, such adhesive may be any suitable medical-grade pressure-sensitive adhesive. The catheter depicted for illustrative purposes in this application is essentially the same as the catheter of the aforementioned patent, and reference may be had to such patent for further details of construction and operation. It is to be understood, however, that while FIG. 1 illustrates a catheter of preferred construction, there may be substantial departures from that construction. More specifically, the antimicrobial insert may be used with any of a variety of known elastic (latex rubber) external male catheters, each of which is designed to be adhesively secured to a wearer's penis and is at least provided with a drainage tube portion and an integrally-formed funnel-shaped portion.

Insert 20 is of cup-shaped configuration having an enlarged opening 21 at its proximal end and a reduced opening 22 at its distal end. The thin-walled insert may be formed of any soft, flexible polymeric material capable of serving as a suitable substrate or support for an antimicrobial agent. Polyethylene or ethylene vinyl acetate copolymer are believed particularly effective, but other materials such as silicone rubber or polyurethane may be used. The surfaces of the insert may be smooth and non-porous (as shown) or they may be textured or foraminous (for example, closed-cell polyethylene foam). In any event, the insert should be self-recoverable in shape, in contrast to being limp, and should function to reinforce the tapered funnel portion 12 of the catheter into which it fits. The outside surface of the insert should have essentially the same contour as the inner surface of funnel portion and should function to prevent inward collapse of the soft elastomeric material of the funnel portion.

Means are provided for securing insert 20 in position within funnel portion 12. In the illustration given, such means takes the form of an integral collar 23 which extends axially and distally, flaring outwardly at its distal end to provide an outwardly-projecting annular flange 24. It will be noted from FIGS. 1 and 4 that the collar projects distally from funnel portion 12 into the convoluted drainage tube portion 11 and that flange 24 flares outwardly into the enlargement or convolution 15 to restrain disengagement of the insert. Preferably, the outside diameter of the collar is slightly larger than the inside diameter of the catheter opening through which the collar projects, with the result that the elasticity or recovery forces of the catheter help to hold the insert securely in place. Other collar configurations may be provided, depending on the shape and design of the catheter and, if desired, the means for securing the insert in place may consist of, or at least include, adhesive attachment between the insert's outer surface and the funnel portion's inner surface.

The antimicrobial agent carried by the flexible polymeric insert 20 may be distributed throughout the composition of the insert or may be in the form of a surface (especially inner surface) coating. Any of a wide variety of agents known to have antimicrobial properties may be used such as, for example, 2-bromo-2-nitropropane-1,3-diol, as marketed under the designation "Bronopol" by Angus Chemical, Northbrook, Ill.; 2,6-dimethyl-4-hydroxychlorobenzene, marketed under the designation "Ottasept Extra" by Ferro Corporation, Bedford Chemical Division, Bedford, Ohio; and Microban, a proprietary broad-spectrum antimicrobial agent marketed by Microban Products Co., Winston-Salem, N.C. Both Bronopol and Microban are known to be leachable, broad spectrum antimicrobial agents, the former being commonly used as a preservative in cosmetics, pharmaceuticals, and toiletries, and the latter being used in plastics, non-woven fabrics, and clothing fabrics. Ottasept Extra, on the other hand, is a non-leachable wide-range antimicrobial preservative currently used in cosmetics, soaps, creams, and hand cleaners. We have successfully incorporated all of such agents into an ethylene/vinylacetate (28%) resin suitable for forming the insert for a male external catheter, using a conventional mixer (a Brabender mixer) at temperatures not exceeding 80° C. Viability of the Bronopol and Microban agents was established by zone of inhibition testing run against *E. Coli* and *Staphylococcus Aureus*. In contrast to the other agents, Ottasept Extra is incapable of leaching or migrating and therefore produced no zone of inhibition; however, a bacteriostatic effect is indicated when such material is incorporated in the resin as described.

Other antimicrobial agents that may be successfully incorporated under appropriate conditions are believed to be quaternary ammonium compounds such as dimethylbenzyl ammonium saccharinate or 3(trimethoxysilyl)propyloctadecyldimethylammonium choride; isothiazalones such as 5-chlor-2-methyl-3(2H)-isothiazalone and 2-methyl-3(2H)-isothiazalone, and 1,2-benzisothiazolin-3-one, and parabens, such as N-(5-nitro-2-furfurylidene)-1-aminohydantoin, and N-(hydroxymethyl)-N-(1,3 dihydroxy methyl-2,5-dioxo-4-imidazolidinyl)-N-(hydroxy methyl) urea.

Alternatively, such antimicrobial agents may be combined with suitable carriers and applied to the insert element in the form of a coating. Such coatings may be sprayed, dipped, painted, or applied in any other suitable manner. Any flowable materials capable of serving as carriers and binders for the antimicrobial agents may be used, including silicones, polyurethanes, and well-known film-forming agents.

The antimicrobial insert 20 may be inserted into the catheter during manufacture or later at the time of use. It is to be understood that the catheter would be supplied to the user in rolled form (see U.S. Pat. No. 4,626,250) and, with the catheter in rolled condition, the insert 20 may be easily advanced into position within funnel portion 12. With the insert secured in place, the catheter is then ready to be fitted upon a user simply by unrolling the sheath over the penis into the position shown in FIG. 4. The stem of portion 11 is then connected to a suitable drainage tube (not shown) leading to a conventional collection receptacle. A direct fluid pathway therefore exists from the urethral meatus 30 to the collection receptacle, such pathway extending through insert 20 and drainage tube portion 11. Although the existence of such a pathway also creates the possibility that bacteria might migrate in the reverse direction, insert 20 is disposed along the route of such possible migration, thereby eliminating or reducing the risks of patient infection.

Figure 4:
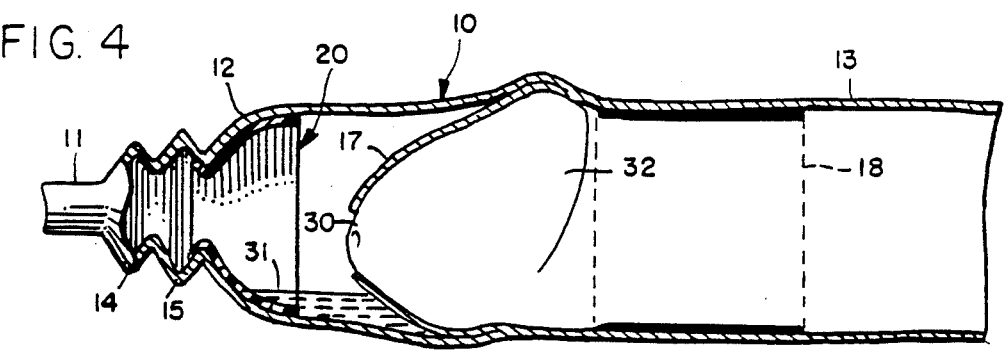
FIG. 4 is a longitudinal cross sectional view illustrating the catheter and insert of FIG. 1 as worn by a patient.

FIG. 4 also depicts a small amount of residual fluid 31 in catheter 10 just distal to the glans 32 of the patient. Sleeve 17 is stretched over the glans and protects its proximal surfaces from contact with such fluid; however, the urethral meatus remains exposed to such contact. It will be noted, however, that fluid 31 also contacts the inner surface of bioactive insert 20, allowing the antimicrobial agent of the insert to kill or at least inhibit microorganisms that might otherwise produce urinary tract infection.

Figure 5:
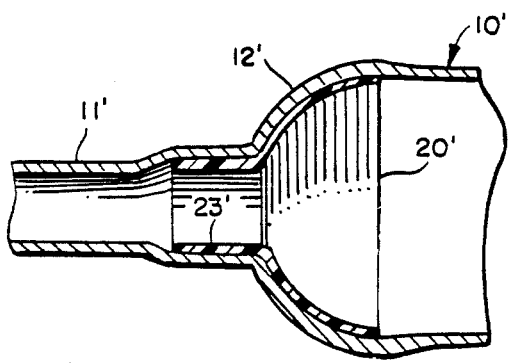
FIG. 5 is a fragmentary longitudinal sectional view illustrating a modified insert and catheter construction.

In the embodiment illustrated in FIG. 5, insert 20' is similar to the insert already described except that the distal collar portion 23' is generally cylindrical. Also, the catheter 10' lacks the convolutions or enlargements 14, 15 of the preceding embodiment. The insert 20' is nevertheless securely held in place because the outside diameter of the cylindrical insert 23 is larger than the inside diameter of drainage tube portion 11' in its unstretched state. FIG. 5 shows the proximal end of the drainage tube portion 11' stretched outwardly about collar 23' and, because of the forces of elastic recovery exerted by portion 11', the insert is secured against axial (proximal) displacement.

While in the foregoing, embodiments of the invention have been disclosed in considerable detail for purposes of illustration, it will be understood by those skilled in the art that many of these details may be varied without departing from the spirit and scope of the invention.

We claim:

1. A male external catheter formed of elastomeric material and including a drainage tube portion and an integral funnel portion communicating with said drainage tube portion; and means for securing said catheter to the penis of a wearer; wherein the improvement comprises a flexible plastic insert disposed within said funnel portion; said insert being cup-shaped with an enlarged opening at one end and a reduced opening at its opposite end; an antimicrobial agent provided by said insert for at least inhibiting bacterial growth in urine contacting said insert within said catheter; and retaining means for retaining said insert within said funnel portion; said retaining means comprising a collar portion of said insert extending into and frictionally engaging the interior of said drainage tube portion; said drainage tube portion including a bulbous enlargement; said collar portion having an integral annular flange flaring outwardly within said enlargement for holding said insert in placed within said catheter.

2. The catheter of claim 1 in which said insert is formed of polyethylene.

3. The catheter of claim 1 in which said insert is formed of ethylene vinyl acetate copolymer.

4. A male external catheter formed of elastomeric material and including a drainage tube portion and an integral funnel portion communicating with said drainage tube portion; and means for securing said catheter to the penis of a wearer; wherein the improvement comprises a flexible plastic insert disposed within said funnel portion; said insert being cup-shaped with an enlarged opening at one end and a reduced opening at its opposite end; an antimicrobial agent provided by said insert for at least inhibiting bacterial growth in urine contacting said insert within said catheter; and retaining means for retaining said insert within said funnel portion; said means for securing said catheter to a wearer comprising a generally cylindrical body portion of said catheter integral with said funnel portion and extending from one end of said funnel portion; said catheter also including a tapered inner sleeve within said cylindrical body portion; said sleeve tapering towards said insert and terminating at a spaced distance axially from said insert; said sleeve being stretched tightly over the glans with said insert spaced axially in front of the urethral meatus when said catheter is worn by a user.

5. The catheter of claim 4 in which said retaining means comprises a collar portion of said insert extending into and frictionally engaging the interior of said drainage tube portion.

6. The catheter of claim 5 in which said collar portion has an outside diameter larger than the inside diameter of said drainage tube portion in an unstretched state.

7. The catheter of claim 6 in which said collar portion is generally cylindrical in shape.

8. The catheter of claim 4 in which said insert is formed of polyethylene.

9. The catheter of claim 4 in which said insert is formed of ethylene vinyl acetate copolymer.

* * * * *